US008864766B2

(12) United States Patent
Weaver

(10) Patent No.: US 8,864,766 B2
(45) Date of Patent: Oct. 21, 2014

(54) KERRISON RONGEURS

(76) Inventor: Edgar Weaver, Roanoke, VA (US)

(*) Notice: Subject to any disclaimer, the term of this patent is extended or adjusted under 35 U.S.C. 154(b) by 523 days.

(21) Appl. No.: 13/038,056

(22) Filed: Mar. 1, 2011

(65) Prior Publication Data
US 2011/0213369 A1 Sep. 1, 2011

Related U.S. Application Data

(60) Provisional application No. 61/339,150, filed on Mar. 1, 2010.

(51) Int. Cl.
*A61B 17/16* (2006.01)

(52) U.S. Cl.
CPC .................................. *A61B 17/1611* (2013.01)
USPC ........................................................... 606/83

(58) Field of Classification Search
CPC ........... A61B 17/1604; A61B 17/1606; A61B 17/1608; A61B 17/1611
USPC ........ 606/79, 83, 184; 30/182, 184, 214, 242; 600/562, 564; 227/180.1
See application file for complete search history.

(56) References Cited

U.S. PATENT DOCUMENTS

| | | | |
|---|---|---|---|
| 3,507,284 A | 4/1970 | Simmons et al. | |
| 4,777,948 A | 10/1988 | Wright | |
| 4,990,148 A * | 2/1991 | Worrick et al. | 606/83 |
| 5,026,375 A * | 6/1991 | Linovitz et al. | 606/79 |
| 5,273,519 A * | 12/1993 | Koros et al. | 606/83 |
| 5,582,618 A * | 12/1996 | Chin et al. | 606/170 |
| 5,766,177 A * | 6/1998 | Lucas-Dean et al. | 606/83 |
| 5,873,886 A * | 2/1999 | Larsen et al. | 606/180 |
| 6,142,997 A * | 11/2000 | Michelson | 606/83 |
| 6,478,805 B1 | 11/2002 | Marino et al. | |
| 6,520,979 B1 * | 2/2003 | Loubens et al. | 606/205 |
| 7,850,694 B2 * | 12/2010 | Raus | 606/84 |
| 8,377,082 B2 * | 2/2013 | Clague et al. | 606/159 |
| 2004/0122433 A1 * | 6/2004 | Loubens et al. | 606/83 |
| 2005/0267503 A1 | 12/2005 | Hunstad | |
| 2007/0265633 A1 | 11/2007 | Moon et al. | |
| 2008/0221383 A1 | 9/2008 | Way et al. | |
| 2011/0213369 A1 * | 9/2011 | Weaver | 606/83 |
| 2012/0016402 A1 * | 1/2012 | Weisshaupt et al. | 606/184 |
| 2013/0041379 A1 * | 2/2013 | Bodor et al. | 606/83 |

* cited by examiner

*Primary Examiner* — Todd Manahan
*Assistant Examiner* — Eric S Gibson
(74) *Attorney, Agent, or Firm* — Ober, Kaler, Grimes & Shriver; Royal W. Craig

(57) ABSTRACT

A Kerrison rongeur employing a shearing/cutting or grasping mechanism, and suited for specific cutting and sampling bone, cartilage and soft tissue. A slideable upper member has on its advancing face a cutting element that moves past an opposing cutting element on a stationary footplate to produce a shearing action of tissue positioned within the jaws. The cutting element of the slideable member may move past the stationary member on the outside in an overbite situation or on the inside in an underbite situation. A hybrid over/underbite jaw is also contemplated along with a guillotine cutting element and a textured grasping element. In operation, the tissue is placed between the jaw and footplate, and the former is advanced towards the latter to cut and/or grasp and remove for a surgical site.

1 Claim, 5 Drawing Sheets

KERRISON RONGEURS

CROSS REFERENCE TO RELATED APPLICATIONS

The present application derives priority from provisional application 61/339,150 filed on Mar. 1, 2010 which is incorporated herein by reference.

BACKGROUND OF THE INVENTION

1. Field of the Invention

The present invention relates generally to surgical instruments and, more particularly, to improved Kerrison type rongeurs for cutting or sampling bone, cartilage and soft tissue.

2. Description of the Background

Rongeurs and similar surgical tools have been known and employed by surgeons for gouging away bone and remove tissue or any other biological material (collectively tissue) during surgical operation. Kerrison type rongeurs are used during spinal surgery to remove bone, cartilage and soft tissue from the spinal posterior in order to gain access into the spinal canal. Such rongeurs typically have a moveable jaw that closes against a stationary anvil or foot plate. In use, a surgeon places bone to be cut between the jaw and foot plate, and squeezes the handle of the rongeur to advance the jaw through the bone to the foot plate, thereby amputating that portion of bone. Typically, the foot plate is flat and the jaw is provided with peripheral cutting edges that bear directly against the flat foot plate at completion of the cutting motion. This guillotine type cutting mechanism, however, has inherent deficiencies. For example, the compression-type cut often results in splintering or fragmentation of the bone which may be lost or dispersed into the surgical site. Additionally, the removed bone or tissue is compacted into jaw, potentially jamming the mechanism of the jaw preventing further motion becoming extremely difficult to remove after each cut. These and other issues with the traditional design have led to numerous alternative approaches to rongeur design.

For example, published U.S. Patent Application No. 2008/0221383 by Bryce Way et al. published Sep. 11, 2008, discloses a tissue excision device comprising a tubular cutting member having a cutting edge at its upper distal end. The tubular cutting member slidably receives a tissue/bone capture member. Near the distal end of the tissue capture member is a radial recess defined by a distal shoulder. In use, the tissue capture member proximally slides within the tubular cutting member, and the top edge of the distal shoulder and the cutting edge of the cutting member, in combination, shear the tissue placed within the recess.

Published U.S. Patent Application No. 2007/0265633 by Jon Kenneth Moon et al. published Nov. 15, 2007, shows a device for removing nucleus pulposus. The device comprises a hollow cutting tube having a cutting edge at its distal end. Reciprocally mounted within the cutting tube is a cylindrical collection tube having an aperture proximate to its distal end. The periphery of the aperture is a cutting edge. In use, the device is positioned so that the nucleus pulposus is inserted within the aperture. The cutting tube then slides over the aperture shearing the nucleus pulposus between the cutting tube's cutting edge and the aperture's periphery.

Published U.S. Patent Application 2005/0267503 by David L. Hunstad published Dec. 1, 2005, teaches a rongeur comprising a base and a slidably connected barrel. At the distal end of the base is footplate, and extending proximally from the footplate is a plunger. The barrel defines a hollow chamber. The plunger is shaped to closely fit within the chamber's opening, and the plunger has sharpened peripheral edges. In use, the barrel is distally advanced so that the chamber receives the plunger, thereby shearing the tissue there between.

U.S. Pat. No. 6,478,805 to James F. Marino at al. issued Nov. 12, 2002, shows a device for removing cut tissue comprising a stationary tubular barrel having an aperture proximate to its distal end. Reciprocally mounted within the stationary tubular barrel is a tubular cutting element with a cutting edge around the distal circumference. To sever tissue, the tissue is inserted within the aperture, and the tubular cutting element is advanced in the distal direction. The cutting element's leading edge shears the tissue against the aperture's periphery.

U.S. Pat. No. 5,582,618 to Albert K. Chin et al. issued Dec. 10, 1996, discloses a rongeur having a fixed inner cutting member terminating with a foot plate at the distal end. The upper, proximal edge of the foot plate comprises a cutting edge. Enclosing the inner cutting member is an outer, tubular cutting member, which has a cutting edge at is distal end. In operation, the outer cutting member translates forward to cover the foot plate, and in the process, the tissue is sheared. The footplate is shaped and dimensioned to closely fit within the opening of the outer tubular member so as to shear tissue placed between the distal end of the outer cutting member and the foot plate.

U.S. Pat. No. 4,777,948 to David W. Wright issued Oct. 18, 1988, shows a rongeur comprising a fixed tubular barrel and cutting element having a cutting edge at its distal end. Slidably mounted within the barrel and cutting element is a rod member. Near the distal end, the rod member has a recess that forms a distal shoulder. In use, the rod member is drawn into the barrel, which shears the tissue by trapping the tissue between the distal shoulder and the cutting edge on the cutting element.

U.S. Pat. No. 3,507,284 to Leonard Simmons et al. issued Apr. 21, 1970, teaches a surgical bone cutter comprising a flat fix blade bar. At the distal end of the fix blade bar is a cutting area having an aperture. The periphery of the aperture is interrupted by a cut-away portion that extends from the outer edge of the blade bar to the inner periphery of the aperture. The inner periphery of the aperture has a cutting edge. Reciprocally mounted flush with the fixed blade bar is a movable cutting blade bar. At the distal end of the blade bar is a concave recess. The contour of the recess serves as a cutting edge. In operation, the bone is slide through the cut-away portion into the aperture. The movable blade bar is slid over the aperture, shearing the bone between the blade bar's concave cutting edge and the aperture's cutting edge.

Despite the foregoing, there remains a need for a Kerrison type rongeur that is capable of cutting bone and tissue by a shearing action to avert the problems associated with conventionally designed rongeurs. Such shearing type cutters would include an edge that passes in close and overlapping proximity to the footplate, thereby giving a scissoring effect and resulting in a cleaner cut.

SUMMARY OF THE INVENTION

It is, therefore, a primary object of the present invention to provide a Kerrison type rongeur that is capable of cutting by a shearing action.

It is another object to provide a variety of Kerrison type rongeurs each employing a different shearing/cutting or grasping mechanism and each suited for specifically cutting or sampling bone, cartilage and soft tissue in varying surgical situations.

In accordance with the foregoing objects, the present invention is a surgical rongeur of the Kerrison type that has a shearing mechanism for separating a piece of tissue from the attached structure. The rongeur comprises a movable jaw and stationary footplate having opposing cutting edges. The cutting edges pass closely either inside each other or outside each other to produce a shearing action. In operation, the tissue is placed between the jaw and footplate, and the jaw is advanced towards the footplate. The edge on the jaw passes in a close and progressively overlapping relationship to the footplate, thereby shearing the tissue. In the context of an otherwise traditional rongeur this may be accomplished by a variety of different cutting configurations disclosed herein.

BRIEF DESCRIPTION OF THE DRAWINGS

Other objects, features, and advantages of the present invention will become more apparent from the following detailed description of the preferred embodiments and certain modifications thereof when taken together with the accompanying drawings in which.

DETAILED DESCRIPTION OF THE PREFERRED EMBODIMENT

Figure 1:
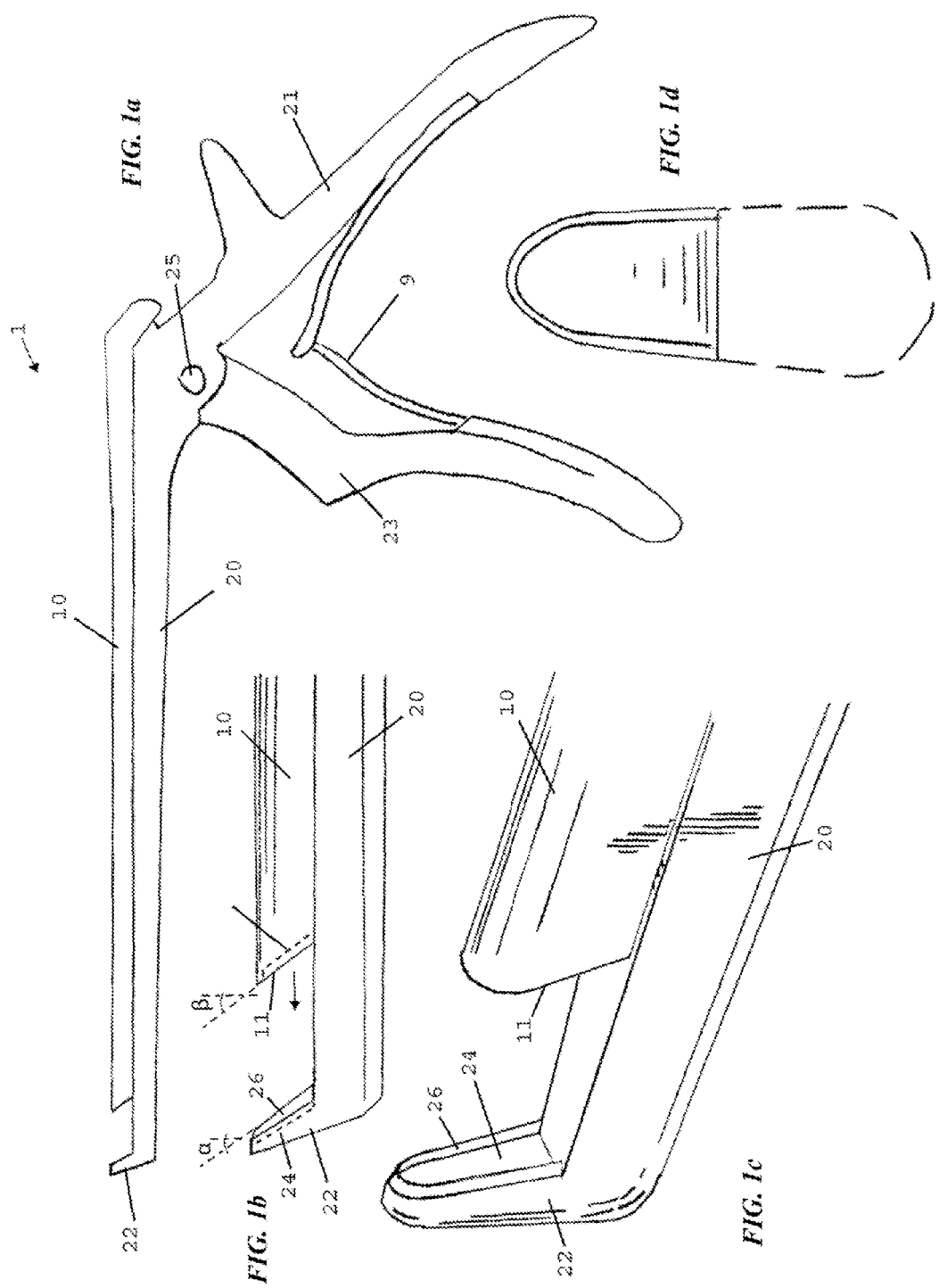
FIG. 1a is a side view of a Kerrison rongeur with an under bite shearing mechanism.
FIG. 1b is a detail view of the cutting edge of a Kerrison rongeur with an under bite shearing mechanism.
FIG. 1c is a perspective view of the cutting edge of a Kerrison rongeur with an under bite shearing mechanism.
FIG. 1d is a section view of a Kerrison rongeur with an under bite shearing mechanism.

The present invention is a surgical rongeur 1 of the Kerrison type that employs a shearing mechanism for more easily cutting and separating a piece of tissue from the attached structure. A tissue-grasping rongeur with textured jaw and footplate is also disclosed. With reference to FIG. 1 for example, each of the rongeurs disclosed herein includes a lower base member 20 having a pistol grip handle 21 at its proximal end rigidly affixed via the longitudinal lower base member to a footplate 22 at its distal end. The base member 20 forms the chassis to which all other elements are affixed. The handle end is gripped by the surgeon while the distal end is inserted into the surgical site as will be described. The footplate 22 may extend laterally from the longitudinal member in any direction but, as depicted, commonly extends upward at an angle from the longitudinal axis, as will also be described. An actuator handle 23 is pivotally affixed to the base member 20 by a screw or rivet 25 and is engaged with the upper member 10 which is slideably engaged in the depicted case to the upper surface of the lower base member 20 opposite the stationary footplate 22. It should be noted that the terms "upper" and "lower" as used herein are used in reference to the depictions of the figures and are not meant to limit the disclosure. The upper member 10, also a longitudinal member, is provided at it distal end with a cutting element 11 and is engaged by the actuator handle 23 such that squeezing the actuator handle against the grip handle drives the upper 10 along the upper surface of the lower member 20 thereby advancing the cutting element 11 toward the footplate 22. A spring mechanism between the handles reverses the motion when the grip is released.

FIGS. 1a through 1d depict a Kerrison rongeur in which the cutting tip and footplate are cooperatively formed to produce an "under bite" shearing mechanism in which the cutting element 11 is received within the footplate 22. This rongeur embodiment comprises a handle assembly as described above operable to slide the upper member 10 relative to the elongate stationery lower member 20 so as to advance the cutting tip or element 11 to the footplate 22. The footplate 22 presents a face consisting of a surface 24 that is recessed relative to a raised perimeter cutting element 26. The cutting element 26 is a blade formed by a bevel on the outside surface of the raised perimeter that tapers inward to a cutting edge at the inner surface of the raised perimeter. The face, i.e. the recessed surface 24 and perimeter cutting element 26, is inclined at an angle offset from the vertical in the plane including the longitudinal axis of the lower base member 20. The incline angle $\alpha$ is preferably approximately 20-30 degrees offset from vertical in the direction away from the top member 10 although it maybe steeper or shallower and may be oriented toward the upper member 10 if the direction of the incline of the cutting element 11 of the upper member 10 is cooperatively inclined as will be described. It should be understood that the term "vertical" as used herein is not intended to be limiting and refers to the direction perpendicular to the longitudinal axis of the lower member in which the footplate protrudes. In the depicted example the bottom member is depicted with the longitudinal axis in a left-right orientation on the page (the horizontal) and the footplate protrudes toward the top of the page. Thus the vertical is a line perpendicular to the horizontal toward the top of the page.

The cutting element 11 of the upper member 10 is formed by a peripheral edge around the leading face of the advancing upper member and surrounding a recessed center 29. The peripheral edge of the cutting element is a blade formed by a bevel on the inside surface of the raised perimeter that tapers outward to a cutting edge at the outer surface of the leading face of the upper member. The shape of the upper member 10 at the cutting element 11 is matched by the shape of the recessed surface 24 in the footplate 22. The upper member 10 is sized at the cutting tip to be closely receive within the recess of the footplate 22 formed within the cutting element 26 such that when the handle 23 is gripped to advance the upper member 10 to the footplate 22 the blade of the cutting element 11 at outside surface of the upper member 10 passes closely by the blade at the inner surface of the cutting element 26 until it reaches the recessed surface 24. The close passage of the two blades of the cutting elements 11 and 26 serve to shear any bone or tissue material situated within the jaws of the rongeur. Additionally, the cutting element 11 of the leading face of the upper member 10 is inclined at a slightly lesser angle β than the footplate 22 and its cutting edge 26, preferably an approximately 5 degrees differential such that the cutting element 11 forms a 15-25 degree angle with the vertical. Consequently, when advanced the cutting element 11 first passes the blade of the cutting element 26 at the base of the footplate. At the top member 10 is advanced the point of engagement travels up the blade of the cutting element 26 until it reached the very top of the blade when the top member 10 is fully received within the recess of the foot plate. This advancing shear point concentrates the forces applied by the surgeon via the handle 23 and permits the ronguers to cut or shear significantly more or stronger material. Cooperatively, the recess of the foot plate and the upper member 10 form a void in which sheared bone or tissue material are captured for removal from the surgical site.

In operation, tissue (bone, cartilage or soft tissue) is placed in the jaws of the rongeur, i.e. between the cutting element 11 and the footplate 22 and handle 23 is squeezed to advance the upper member to the foot plate 22. The cutting elements 11, 26 of the upper member and footplate 22 pass in close proximity, progressively overlapping, in a scissoring relationship to shear the tissue. This "under bite" scissoring and shearing action greatly improves the cutting effectiveness and safety of the rongeur. One skilled in the art will readily understand that the overall shape and dimensions of the upper member 10 cutting element 11 and the footplate 22 may be varied as desired provided that their relative form and dimensions remain consistent.

FIGS. 2a through 2d depict a Kerrison rongeur in which the cutting tip and footplate are cooperatively formed to produce an "overbite" shearing mechanism in which the cutting tip or element 34 of the upper member moves outside of and past the cutting element 44 of the foot plate 42 when advanced for cutting. As above, this rongeur embodiment comprises a handle assembly operable to slide the upper member 30 relative to the elongate stationery lower member 40 so as to advance the cutting tip or element 34 to the footplate 42. The footplate 42 again presents a face consisting of a surface 44 that is recessed relative to a raised perimeter cutting element 46. The cutting element 46 is a blade formed by a bevel on the inside surface of the raised perimeter that tapers outward to a cutting edge at the outer surface of the raised perimeter. The face, i.e. the recessed surface 44 and perimeter cutting element 46, is inclined at an angle offset from the vertical in the plane including the longitudinal axis of the lower base member 40. The incline angle α is preferably approximately 15-25 degrees offset from vertical in the direction away from the top member 30 although it maybe steeper or shallower and may be oriented toward the upper member 30 if the direction if the incline of the cutting element 34 of the upper member 30 is cooperatively inclined as will be described.

The cutting element 34 of the upper member 30 is formed by a peripheral edge around the leading face of the advancing upper member and surrounding a recessed center 36. The peripheral edge is a blade formed by a bevel on the outside surface of upper member 30 that tapers inward to a cutting edge 34 at the inner surface of the leading face of the upper member 30. The shape of the upper member 30 at the cutting element 34 is matched by the shape of outside surface of the footplate 42 at the cutting element 46. The upper member 30 is sized at the cutting tip to closely pass outside the cutting element 46 of the footplate 42 such that when the handle 23 is gripped to advance the upper member 30 to the footplate 42 the blade of the cutting element 34 at inside surface of the upper member 30 passes closely by the blade at the outer surface of the cutting element 46. This close passage of the two blades of the cutting elements 46 and 34 serve to shear any bone or tissue material situated within the jaws of the rongeur. Additionally, the cutting element 34 of the leading face of the upper member 30 is inclined at a slightly greater angle β than the footplate 22 and its cutting edge 26, preferably an approximately 5 degrees differential such that the cutting element 11 forms a 20-30 degree angle with the vertical. Consequently, when advanced the cutting element 11 first passes the blade of the cutting element 46 at the top of the footplate. At the top member 30 is advanced the point of engagement travels down the blade of the cutting element 46 until it reached the base of the blade when the cutting element 34 fully passes the cutting element 46 of the footplate. This advancing shear point concentrates the forces applied by the surgeon via the handle 23 and permits the ronguers to cut or shear significantly more or stronger material. Cooperatively, the recess of the foot plate and the upper member 30 form a void in which shear bone or tissue material are captured for removal from the surgical site. This "overbite" scissoring and shearing action greatly improves the cutting effectiveness and safety of the rongeur. The steeper slope of the cutting element 46 of the footplate 42 as compared to the cutting element 34 has the added benefit of tending to grasp tissue placed within the jaws during the cutting process. One skilled in the art will readily understand that the overall shape and dimensions of the upper member 30 cutting element 34 and the footplate 42 may be varied as desired provided that their relative form and dimensions remain consistent.

Figure 3:
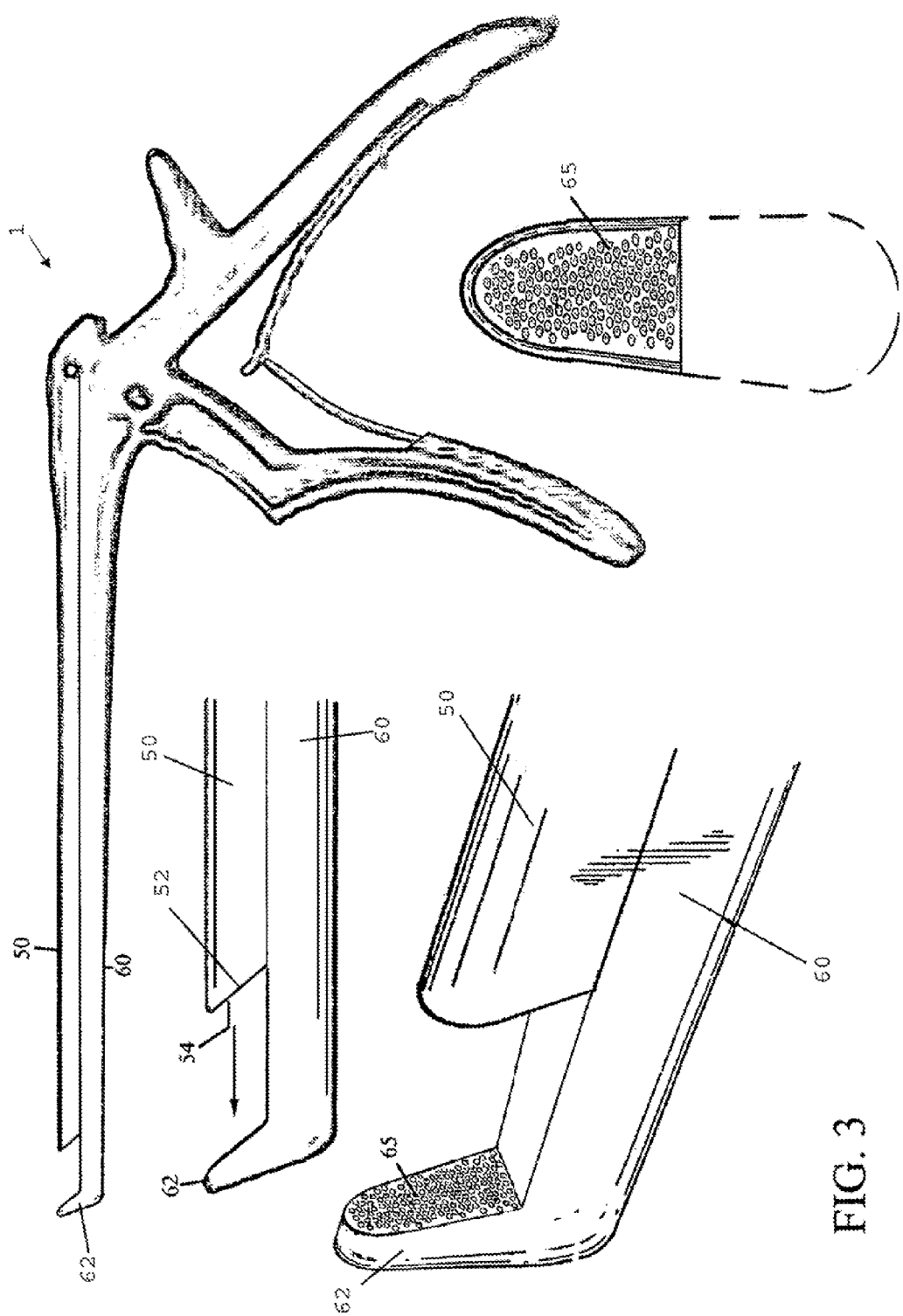
FIG. 3 is a composite perspective view of a Kerrison rongeur adapted for soft tissue grabbing.

FIG. 3 is a composite perspective view of a Kerrison rongeur adapted for soft tissue grabbing. As above, this rongeur embodiment comprises a handle assembly operable to advance an elongate movable upper member 50 that slides atop an elongate stationery lower member 60. The lower member 60 extends to a raised footplate 62, and the upper member extends to an inclined jaw 52. Here the jaw 52 comprises a surface 54 inclined at approximately a 20-30 degree angle offset from vertical. The footplate 62 is sized equally to the jaw 52 and is formed with a textured frontal surface. The textured frontal surface of the footplate 62 is inclined at the same angle as the surface 54 of the jaw 52. Consequently, the surface 54 of the jaw 52 fits flush against the footplate 42. The frontal surface of the footplate 62 may be textured or ridged with suitable surface definitions to improve its gripping ability. The surface definition may be comprised of, for example, a plurality of closely-spaced very fine dimples 65 patterned across the surface. The surface 54 of the jaw 52 may likewise be defined by similar surface defining dimples 65 or, alternatively, both the surfaces of the jaw 52 and that of the footplate 62 may be designed with texture or ridging in such a way that these surfaces seat together. In operation, tissue (bone, cartilage or soft tissue) to be removed is compressed between the jaw 52 and footplate 62, and the textured surface(s) enhance the ability to manipulate or remove the tissue without slippage.

Figure 4:
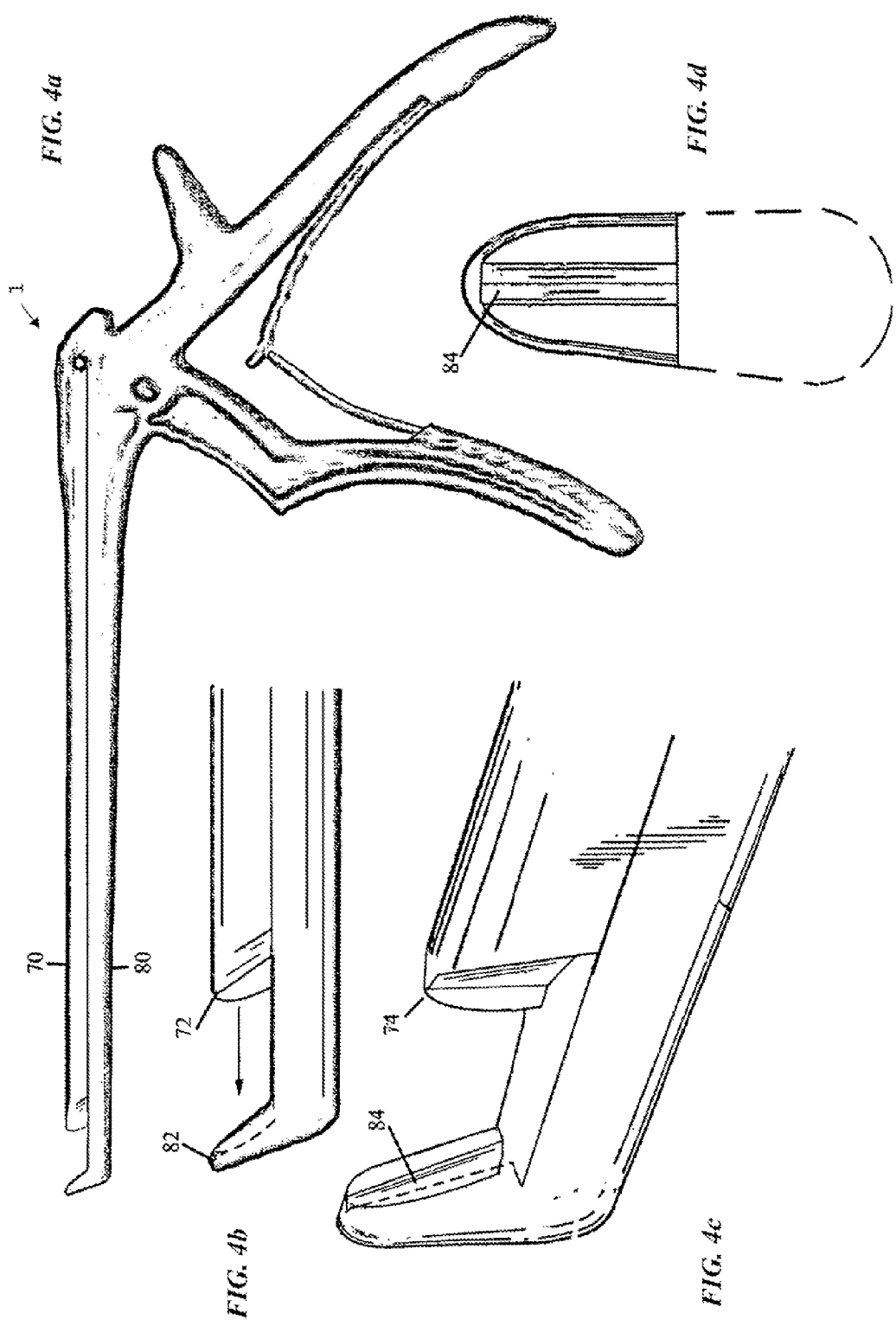
FIG. 4a is a side view of a Kerrison rongeur with a guillotine shearing mechanism.
FIG. 4b is a detail view of the cutting edge of a Kerrison rongeur with a guillotine shearing mechanism.
FIG. 4c is a perspective view of the cutting edge of a Kerrison rongeur with a guillotine shearing mechanism.
FIG. 4d is a section view of a Kerrison rongeur with a guillotine shearing mechanism.

FIGS. 4a through 4d depict a Kerrison rongeur with a guillotine shearing mechanism. Here again the rongeur embodiment comprises a handle assembly operable on an elongate movable upper member 70 that slides atop an elongate stationery lower member 80 to advance a jaw 72 toward an opposing foot plate 82. The lower member 80 extends from the handle assembly to the raised footplate 82. Here the jaw 72 comprises a forwardly-disposed cutting blade 74 oriented vertically, top-to-bottom along the jaw 72 and inclined at approximately a 20-30 degree angle offset from vertical. The cutting blade 74 is symmetrical and slightly rounded in profile from top-to-bottom, as best seen in FIG. 4b. As a result of the rounded profile the leading edge of the jaw 72 is the central portion of the blade 74 which approaches and encounters intervening tissue first as the upper member 70 is advanced. The sides of the upper member 80 that support the blade 74 are beveled back so as not to impede or obstruct the cutting action as the upper member is advanced. The cutting blade 74 of the jaw 72 cooperates with a rounded mating groove 84 formed in the footplate 82 and when fully closed, the cutting blade 74 nests inside the groove 84 of footplate 82. The groove 84 of the footplate 82 is inclined at a steeper angle than that of the blade 74 of the jaw 72, e.g., a 5 degree differential or 15-25 degree angle from the vertical. When advanced to the foot plate the center, leading edge of the blade 74 enters and contact the groove 84 of the footplate 82 first. As a result of the slightly rounded profile of the cutting blade 74 and groove 84 the scissoring action of the blade entering the groove 84 advances both upward to the top of the blade and downward to the bottom of the blade from the initial point of engagement in a true guillotine-type manner. The scissoring action continues until the blade is fully seated in the groove and the jaws against the foot plate at which point the tissue in between is fully resected and can be removed. In operation, tissue (bone, cartilage or soft tissue) is placed between the jaw 72 and footplate 82, and the jaws advanced towards footplate by action of the handle assembly. The blade 74 of the jaw 72 scissors along the groove 84 of the footplate 82, effectively shearing the tissue. This scissoring and shearing action greatly improves the cutting effectiveness of the rongeur. Again, one skilled in the art will readily understand that the overall dimensions of the jaw 72 and footplate 82 may be varied as desired provided that their relative dimensions remain constant.

Figure 2:
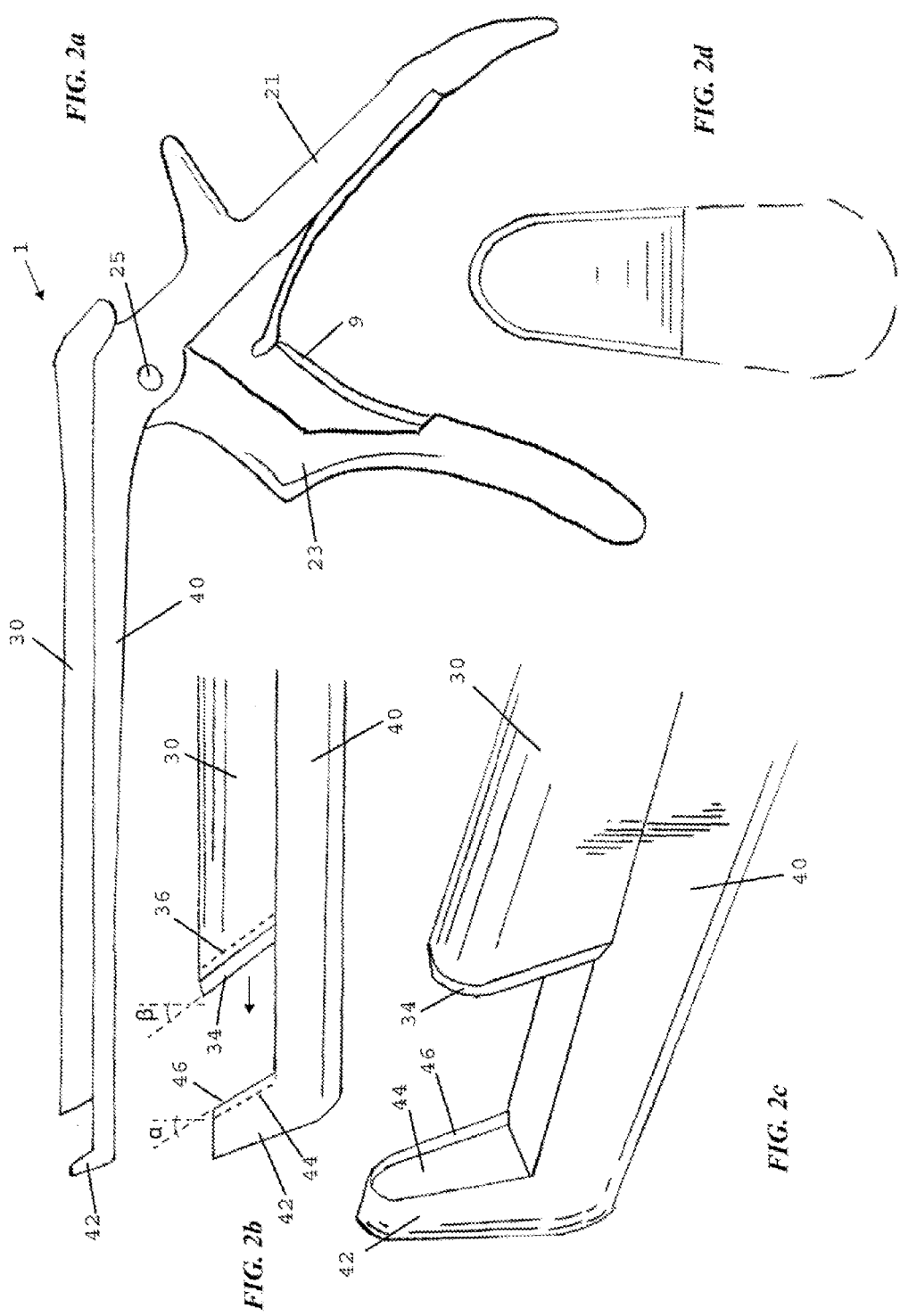
FIG. 2a is a side view of a Kerrison rongeur with an overbite shearing mechanism.
FIG. 2b is a detail view of the cutting edge of a Kerrison rongeur with an overbite shearing mechanism.
FIG. 2c is a perspective view of the cutting edge of a Kerrison rongeur with an overbite shearing mechanism.
FIG. 2d is a section view of a Kerrison rongeur with an overbite shearing mechanism.
Figure 5:
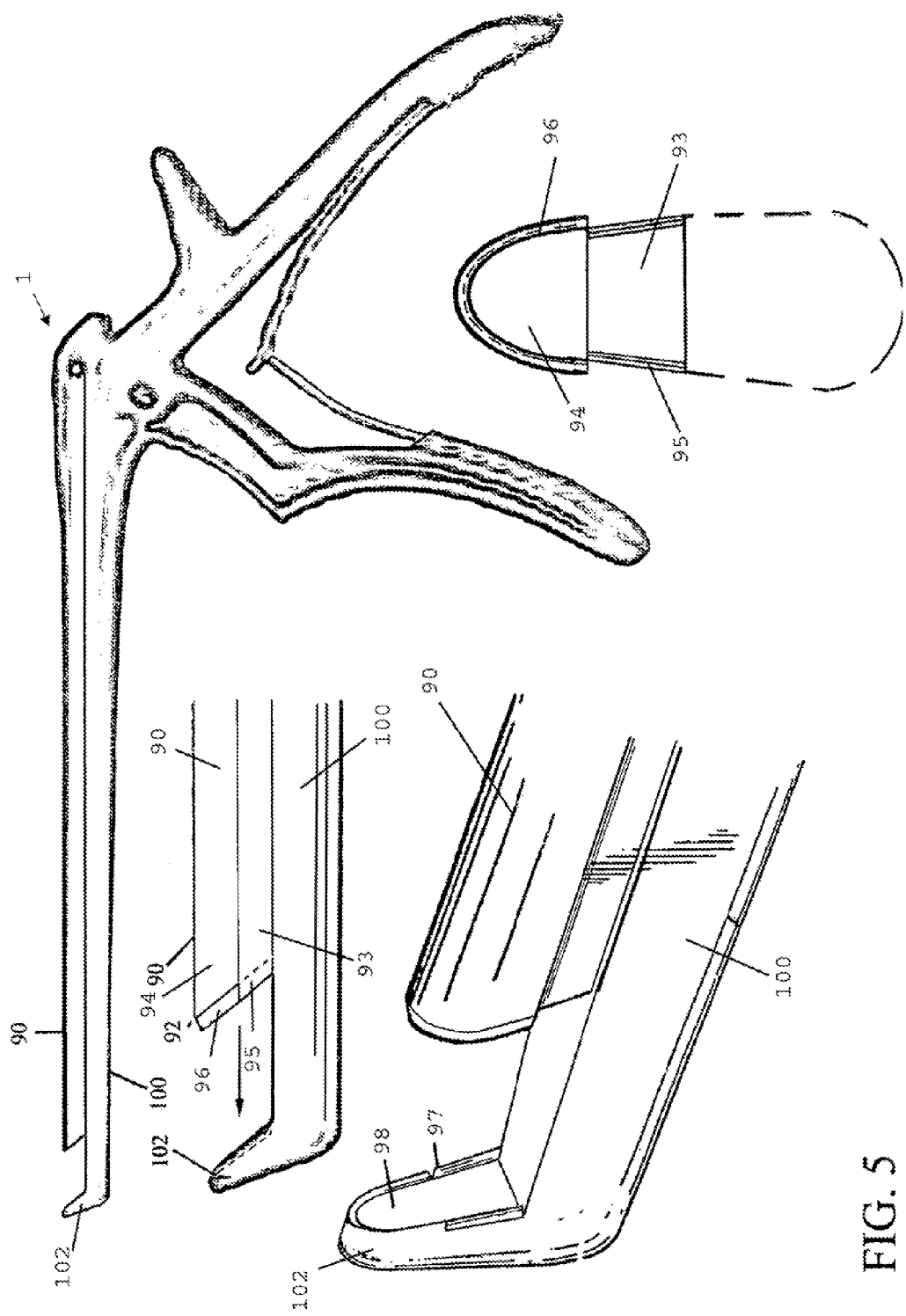
FIG. 5 is a composite perspective view of a Kerrison rongeur with a hybrid shearing mechanism comprising a combination of overbite and under bite.

FIG. 5 is a composite perspective view of a Kerrison rongeur with a hybrid shearing mechanism comprising a combination of the "under bite" and "overbite" mechanisms of the embodiments of FIG. 1 and FIG. 2, respectively This rongeur embodiment incorporates element from both embodiments of FIGS. 1 and 2, likewise comprising a handle assembly operable on an elongate movable upper member 90 that slides atop an elongate stationery lower member 100. The lower member 100 extends to a raised footplate 102, and the upper member 90 extends to an inclined jaw 92. The inclined jaw 92 is a hybrid of the jaws of FIGS. 1 and 2, narrower at its lower/posterior portion 93 with a cutting edge 95 formed by a bevel tapered to the outside edge that is received and seated within the footplate 102 creating an under bite shear as per FIG. 1. The upper portion 94 of the incline jaw 92 is however, wider and longer with a cutting edge 96 formed by a bevel tapered to the inside edge that passes closely over the outside of the footplate thereby creating an overbite shear as per FIG. 2. In this case the over bite portion and under bite portion of the jaw 92 cannot be in continuum due to the different modes of shear so the inclined jaw 92 includes a segue between the over bite portion and under bite portion. Specifically, the lower/posterior 93 under bite edge is truncated about halfway up the jaw 92, and the upper/anterior 94 portion begins at this same place. This essentially forms a two-tier surface on the jaw 92 generally inclined at approximately a 20-30 degree angle offset from vertical. The top tier of the jaw 92 is recessed and the peripheral edges of the jaw 92 in this top tier form an overbite cutting blade 96 that fits overtop the footplate as described. The bottom tier of the jaw 92 is narrower and includes peripheral edges beveled as shown to form the cutting element 95. The footplate 102 is provided with a similar discontinuous perimeter edge 97 around a recessed surface 98 to form cooperative shearing surface for the upper and lower portions of the jaw as seen in the figures. identical to that of FIG. 1. Given that the jaw 92 is inclined at a sharper angle than the footplate 102 (likewise a 5 degree differential), the upper overbite portion of the jaw 92 makes first contact with the footplate 102. The upper tip of the jaw 92 fits overtop the footplate 102 causing a scissoring effect as the peripheral edges of the jaw 92 upper tier slide transversely against the footplate 102. This scissoring or shearing action continues until the lower tier of the jaw 92 seat against the inside of the footplate 102. The lower tiers of jaw 92 and footplate 102 come together, at which point the tissue is fully resected and can be removed. This hybrid rongeur embodiment combines both an over bite and under bite scissoring or cutting action which greatly improves the cutting effectiveness of the rongeur in specific situations. Once again, one skilled in the art will readily understand that the overall dimensions of the jaw 92 and footplate 102 may be varied as desired provided that their relative dimensions remain constant.

It should now be apparent that the above-described variety of Kerrison rongeurs each employ different shearing/cutting or grasping mechanisms each suited for specific cutting or sampling bone, cartilage and soft tissue.

The above-described embodiments are for the purpose of promoting an understanding of the principles of the invention. It should nevertheless be understood that no limitation of the scope of the invention is thereby intended, such alternations and further modifications in the illustrated device, and such further applications of the principles of the invention as illustrated herein being contemplated as would normally occur to one skilled in the art to which the invention relates.

I claim:
1. A Kerrison-type rongeur, comprising:
an elongate chassis having at a proximal end, a handle assembly for gripping by an operator and at a distal end and a footplate protruding therefrom, said footplate having a surface forming a first angle from vertical and comprising a first cutting element, said first cutting element comprising a first perimeter raised around at least a portion of said surface forming a recess therein, said first perimeter comprising a first beveled surface tapered to form a first blade at an outer surface of said first perimeter and a second beveled surface tapered to form a second blade at an inner surface of said first perimeter; and
an elongate upper member slideably affixed to said chassis and engaged at a first end to said handle assembly so as to be advanceable to said footplate by operation of said handle assembly, said upper member further comprising a second cutting element at a second end, said cutting element forming a second angle from vertical that is different from the first angle of said footplate surface, said second cutting element comprising a second perimeter raised around a least of portion of said second end, said second perimeter comprising a third beveled surface tapered to form a third blade at an outer surface of said second perimeter and a fourth beveled surface tapered to form a fourth blade at an inner surface of said second perimeter;
wherein said second cutting element is advanced closely past said first cutting element by operation of said handle assembly such that tissue situated between said cutting elements is resected by a shearing action between said cutting elements, said first blade passing inside said fourth blade and being received within said recess to produce a portion of said shearing action and said sec- ond blade passing outside of said third blade to produce a portion of said shearing action.

* * * * *